(12) United States Patent
Li et al.

(10) Patent No.: US 10,286,104 B2
(45) Date of Patent: *May 14, 2019

(54) METHOD OF PREPARING POROUS CARBONATE APATITE FROM NATURAL BONE

(71) Applicant: Collagen Matrix, Inc., Oakland, NJ (US)

(72) Inventors: Shu-Tung Li, Wyckoff, NJ (US); Hui-Chen Chen, Wayne, NJ (US); Debbie Yuen, Woodcliff Lake, NJ (US)

(73) Assignee: Collagen Matrix, Inc., Oakland, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/450,789

(22) Filed: Mar. 6, 2017

(65) Prior Publication Data

US 2017/0173211 A1   Jun. 22, 2017

Related U.S. Application Data

(63) Continuation of application No. 14/657,557, filed on Mar. 13, 2015, now abandoned, which is a continuation-in-part of application No. 13/248,762, filed on Sep. 29, 2011, now Pat. No. 8,980,328.

(51) Int. Cl.
| | |
|---|---|
| *A61L 27/12* | (2006.01) |
| *A61L 27/56* | (2006.01) |
| *A61L 27/58* | (2006.01) |
| *C01B 25/16* | (2006.01) |
| *C01B 25/32* | (2006.01) |

(52) U.S. Cl.
CPC .............. *A61L 27/12* (2013.01); *A61L 27/56* (2013.01); *A61L 27/58* (2013.01); *C01B 25/16* (2013.01); *C01B 25/32* (2013.01); *A61L 2430/02* (2013.01); *C01P 2002/72* (2013.01); *C01P 2002/82* (2013.01); *C01P 2002/90* (2013.01); *C01P 2006/12* (2013.01); *C01P 2006/80* (2013.01); *C01P 2006/90* (2013.01)

(58) Field of Classification Search
None
See application file for complete search history.

(56) References Cited

U.S. PATENT DOCUMENTS

| | | |
|---|---|---|
| 5,167,961 A | 12/1992 | Lussi et al. |
| 5,417,975 A | 5/1995 | Lussi et al. |
| 6,706,290 B1 | 3/2004 | Kajander et al. |

(Continued)

FOREIGN PATENT DOCUMENTS

WO   WO-2008/032928 A1   3/2008

OTHER PUBLICATIONS

Murugan et al "Scaffolds for Bone Tissue Restoration from Biological Apatite" Trends in Biomaterials and Artificial Organs vol. 20, pp. 35-39, 2006.

*Primary Examiner* — Johann R Richter
*Assistant Examiner* — Casey S Hagopian
(74) *Attorney, Agent, or Firm* — Cesari and McKenna, LLP

(57) ABSTRACT

A carbonate apatite prepared from natural bone. The carbonate apatite has a protein content of 2000-8000 parts per million and a surface area of 15 to 70 m²/g. Also provided is a method for preparing the carbonate apatite from cancellous bone particles.

16 Claims, 2 Drawing Sheets

(56) References Cited

U.S. PATENT DOCUMENTS

| | | | |
|---|---|---|---|
| 6,972,041 B1 | 12/2005 | Stone | |
| 8,298,566 B2 | 10/2012 | Markoulides | |
| 8,980,328 B2 * | 3/2015 | Li | C01B 25/16 |
| | | | 424/549 |
| 2013/0084228 A1 * | 4/2013 | Li | C01B 25/16 |
| | | | 423/175 |

* cited by examiner

METHOD OF PREPARING POROUS CARBONATE APATITE FROM NATURAL BONE

CROSS-REFERENCE TO RELATED APPLICATIONS

The present application is a continuation of U.S. patent application Ser. No. 14/657,557, filed on Mar. 13, 2015, now abandoned, which was filed as a continuation-in-part of U.S. patent application Ser. No. 13/248,762, filed on Sep. 29, 2011 now U.S. Pat. No. 8,980,328. The contents of the prior applications are hereby incorporated by reference in their entirety.

BACKGROUND

Field

This application relates to calcium-containing bone grafting materials.

Background Information

Current synthetic calcium-containing bone grafting materials used clinically include calcium sulfate, calcium carbonate (coral-based), and various calcium phosphate compounds (e.g., tricalcium phosphate, hydroxyapatite). The synthetic calcium-containing materials have the disadvantage of either resorbing too fast (e.g., calcium sulfate) or too slow (e.g., hydroxyapatite), which would negatively impact bone growth and regeneration.

Carbonate apatite is the mineral structure of natural bone. Unlike the highly crystalline structure of hydroxyapatite, carbonate apatite in bone has a lower degree of crystallinity. The lower degree of crystallinity allows the bone to turnover and remodel in vivo, particularly under the influence of mechanical stress conditions. If the mineral can be isolated from natural bone without significantly changing its structure, it would be a more suitable bone grafting material.

Methods for preparing mineral from natural bone include those using organic solvents (e.g., ethylenediamine) under reflux conditions (see, e.g., U.S. Pat. Nos. 2,938,593; 5,167,961; and 5,417,975), and those using heat treatment at a temperature generally higher than 900° C. (see, e.g., U.S. Pat. No. 4,654,464). These methods have various disadvantages, such as generating toxic solvent waste, altering the structure of the bone mineral, and making bone mineral that causes tissue reactions. See, e.g., Gardner, A. F., J. Oral. Surg. Anesth. Hosp. Dent. Serv., 1964, 22:332-40.

There is a need for a method that generates commercial quantities of highly porous, biocompatible, and bioresorbable carbonate apatite from natural bone without significantly changing the structure of the mineral phase and that will not generate toxic waste.

SUMMARY

This invention is based on the unexpected discovery of a method capable of generating large quantity of porous carbonate apatite for various medical and dental surgical applications.

Accordingly, described herein is a method of preparing carbonate apatite from natural bone. The method includes obtaining cancellous bone particles; treating the bone particles with hot water and an organic solvent; repeating the treating step at least once; drying the bone particles; and heating the bone particles at 500° C. to 620° C. for 10 to 50 hours.

To obtain the bone particles, a cancellous bone can be first cleaned to remove adhering tissues, attached cartilages and cortical bone. The bone can then be grounded into particles having a size ranging from about 2 mm to about 15 mm, preferably from 5 mm to 10 mm. Uniformity of the size of the bone particles can facilitate the removal of loosely associated organic moieties from the bone (e.g., cells, cell debris and blood components). The hot water and organic solvent (e.g., ethanol and isopropanol) treatments serves to remove organic materials not directly associated with the bone (e.g., lipids, blood components, cells and debris). The thusly prepared bone particles can then be heated at a specific temperature range for a period of time (e.g., 10 to 50 hours). In some embodiments, the bone particles are heated at 500° C. to 620° C., preferably between 570° C. to 610° C., and more preferably between 590° C. to 605° C.

The carbonate apatite prepared from natural bone can have a surface area of 15 to 70 $m^2/g$ and a protein content of 2000-8000 parts per million. The carbonate apatite can also have a carbonate content of 1 to 7% and a degree of crystallinity of 45 to 65%.

The details of one or more embodiments of the invention are set forth in the accompanying drawing and the description below. Other features, objects, and advantages of the invention will be apparent from the description and drawing, and from the claims. All references cited herein are hereby incorporated by reference in their entirety.

BRIEF DESCRIPTION OF THE DRAWINGS

The invention description below refers to the accompanying drawings, of which.

DETAILED DESCRIPTION

Figure 1:
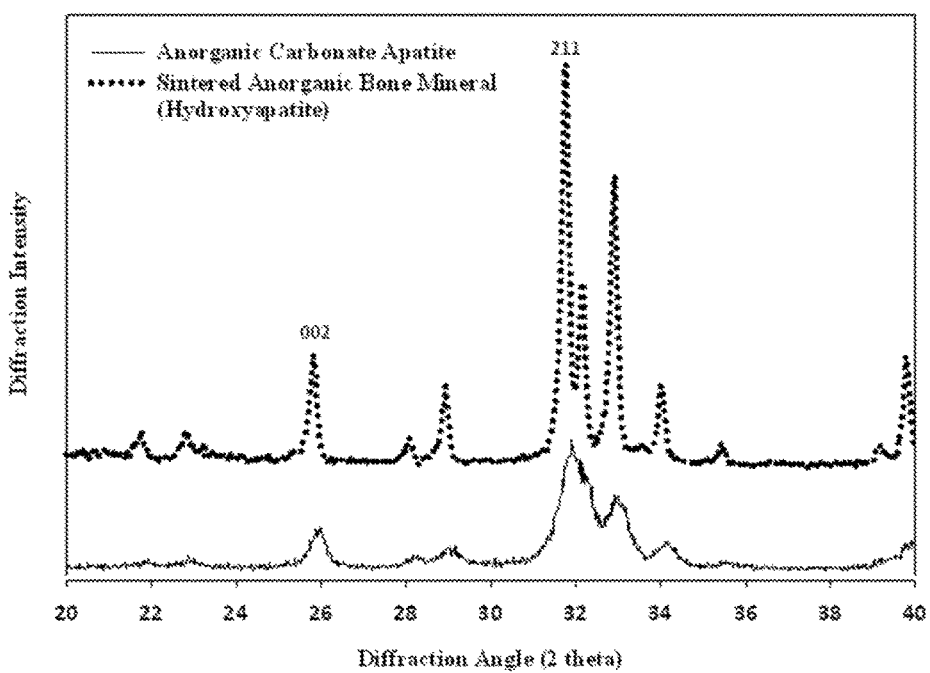
FIG. 1 is a graph showing an X-ray diffraction pattern of sintered anorganic bone mineral (hydroxyapatite) and anorganic carbonate apatite.

This invention relates to a method of preparing carbonate apatite mineral from natural bone of mammals that has a structure substantially similar to the mineral of the intact bone. Particularly, the method generates highly porous carbonate apatite from epiphysis of the mammals. Fresh epiphysis, the expanded head of bone containing mainly cancellous (spongy) bone tissue, is the main source of bone tissue harvested and provided by suppliers. Since the spongy bone has pore sizes generally in the range of 50 µm to 700 µm, it is the ideal structure for bone conduction and new bone growth.

The method described herein involves cleaning and processing of spongy bone to remove organic components associated with bone, leaving the intact mineral crystal component (carbonate apatite) for bone conduction and growth applications. More specifically, the method includes heating thoroughly cleaned bone particles under well controlled temperature and time ranges that will not cause significant phase transition from low crystalline carbonate apatite structure to high crystalline hydroxyapatite.

Generally, the carbonate content of the carbonate apatite prepared from the method is in the range of about 1% to about 7% and the degree of crystallinity ranges from about 45% to about 65%. High crystalline hydroxyapatite has no carbonate and has a degree of crystallinity generally greater than 98%. Thus, carbonate apatite has smaller-sized crystals and less perfect crystal lattice than hydroxyapatite. The clinical significance of carbonate apatite is that it has a structure similar to that of mineral in intact bone. Thus, when carbonate apatite is implanted, it will behave more similarly to native bone mineral, i.e., allowing turnover or remodel in vivo upon new bone regeneration.

To practice the method, the cortical portion of bone, including periosteum, adhering soft tissues and attached cartilage tissues, is first removed and the spongy bone grounded into particles. The size of the particles is generally in the range of 2 mm to 15 mm, preferably in the range of 5 mm to 10 mm. The ground bone particles are first washed with cold water to remove some blood and marrow components associated with spongy bone. The washed bone particles then go through at least two cycles of hot water and organic solvent treatment. Washing with hot water at boiling temperature for, e.g., 2 to 8 hours, is preferred, which can remove a good part of fat moieties, blood and cell debris from the bone. Organic alcoholic compounds can be used to remove lipids and lipoproteins from the bone. Washing with ethanol or isopropanol (e.g., for 16 to 24 hours at room temperature) is effective in this regard. Alcohol in combination with ether can be used in small scales, but alcohol alone is preferred to minimize toxic materials involved in the method.

The cleaned bone particles are then dried (e.g., via air or oven) and heat-treated. The heating treatment can be carried out in a furnace. For example, the bone particles can be placed in crucibles (e.g., large crucibles with about 50 g of particles in each), which are inserted into a commercial furnace (e.g., Thermo Scientific). The amount of cleaned bone particles used can vary depending on the capacity of the furnace. Thus, the production can be scaled up by using larger capacity furnaces that are commercially available.

The temperature of the furnace can be slowly raised to the target temperature in the range of 500° C. to 620° C. within the first hour. Once the temperature has reached the target temperature, the bone particles are heat-treated for a period of 10 to 50 hours, preferably at 570° C. to 610° C. for 20 to 40 hours, and most preferably at 590° C. to 605° C. for 22 to 33 hours. Generally, the duration of the heating treatment is related to the temperature range selected for the treatment. For example, a higher temperature would require a shorter treatment. In any event, the time period selected should be one that is sufficient to effectively remove organic materials from the bone particles.

The thusly prepared carbonate apatite mineral has a structure substantially similar to the mineral in intact bone. The method described in this invention is applicable to all animal bone tissues including but not limited to bovine, porcine, equine, and ovine so long as the bones are cleaned and ground to the size as described.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Preparation of Natural Bone Mineral

Ground bone particles received from supplier were first washed with cold water for 2-4 hours. The washed bone particles were then boiled with water for 8 hours, the water changed every two hours. The hot water-cleaned bone particles were extracted in isopropanol for 18 hours to remove lipids and lipoproteins. The hot water- and isopropanol-cleaning steps were repeated once within the defined time period (8 hours of hot water extraction and 18 hours of isopropanol extraction). The clean bone particles thus prepared were then air-dried or oven-dried for 24 hours.

After drying, approximate 50 g of the clean bone particles were placed in each of four crucibles. The crucibles were transferred into a furnace, and heat-treated at 595° C. for 33 hours. The crucibles were then cooled in the furnace. Six furnaces were calibrated and used simultaneously to produce a large quantity of carbonate apatite, approximately 600 g.

Characterization of the Natural Bone Mineral

Carbonate apatite bone minerals produced by the above procedure were characterized by the following methods.

(1) X-Ray Diffraction

X-ray diffraction (XRD) pattern provides information about the lattice structure, the size of the crystals and the percent of crystallinity of the mineral. XRD analyses were conducted using PHILIPS PW1710 X-ray diffractometer, and scanned from 20 to 40 degrees (2θ scale) to obtain key reflections for the identification of apatite structure.

The XRD pattern of the anorganic bone mineral as prepared above showed typical key mineral reflections at 211 and 002 of highly crystalline hydroxyapatite. See FIG. 1. The broad spectrum of the bone mineral thusly prepared indicated a smaller crystal size as compared to that of sintered hydroxyapatite, which showed a characteristically narrow spectrum and sharper peaks. Also see FIG. 1. Using the Scherer equation, the average crystal size in the 002-direction was estimated to be 29.4 nm for the bone mineral as prepared above, compared to 45.3 nm for hydroxyapatite. The percent crystallinity of mineral of the bone mineral was determined to be 54.2±1.3% (based on an average of 3 lots) as compared to 99% for hydroxyapatite.

(2) Infrared Spectroscopy

Infrared (IR) spectroscopy provides information relating to the structure of a product in terms of its functional groups. The infrared spectra of the samples were obtained from samples prepared as KBr pellets with 10 weight % sample, and using a Fourier transform infrared spectrophotometer (Perkin-Elmer 983G).

Figure 2:
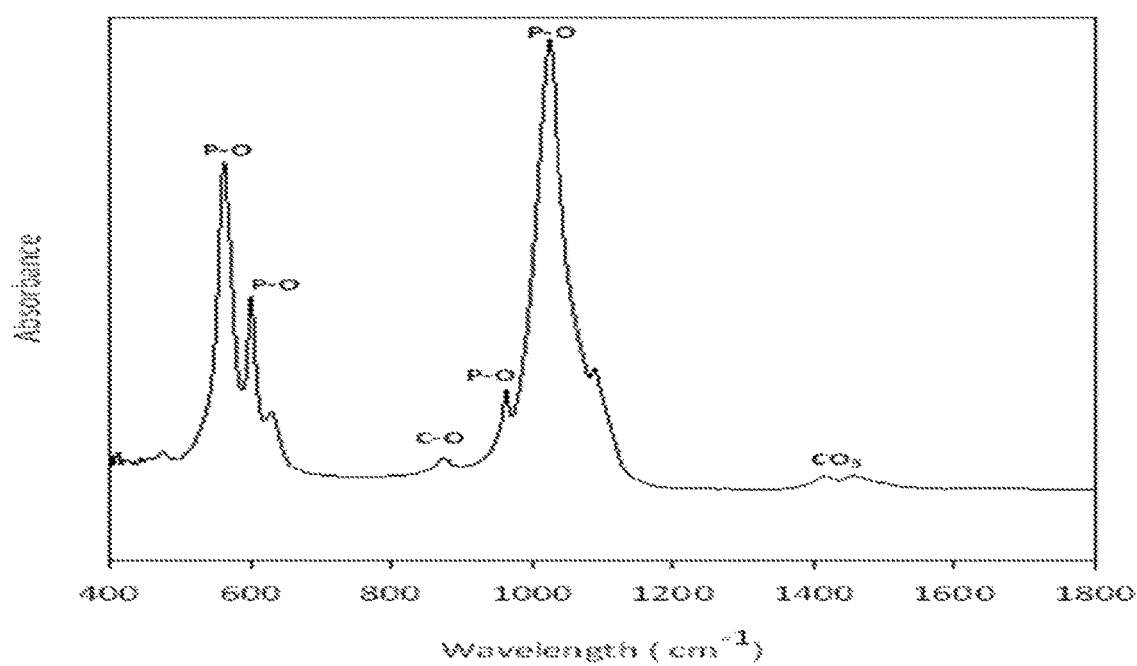
FIG. 2 is a graph showing an infrared spectra of anorganic carbonate apatite.

The IR spectra of the mineral prepared above was similar to the spectra of natural bone consisting of carbonate apatite mineral including: the phosphate ion bands (sharp P-O $\upsilon 4$ antisymmetrical bending mode (550 $cm^{-1}$ to 600 $cm^{-1}$); $\upsilon 3$ antisymmetrical stretching mode (1030 $cm^{-1}$ with 1100 $cm^{-1}$ shoulder); and the carbonate ion ($CO_3$) band ($\upsilon 2$ antisymmetrical stretching mode, 1400 $cm^{-1}$-1500 $cm^{-1}$). See FIG. 2.

The carbonate content in the bone mineral was determined based on a standard curve constructed by establishing the net integration area of carbonate absorption area (923-1332 $cm^{-1}$) to phosphate absorption area (1332-1633 $cm^{-1}$) verses different carbonate content. The bone mineral as prepared above had carbonate content of 2.0±0.3% (average of 3 measurements±S.D.).

(3) Ratio of Calcium to Phosphate

A sample of the mineral bone as prepared above was hydrolyzed in nitric acid to ensure total dissolution of the sample. After cooling, the sample was made up to volume, mixed and diluted for calcium and phosphate analyses by the Inductively Coupled Plasma Chromatography method. Standard solutions of calcium and phosphate were prepared for calculation and correction. It was determined that the bone mineral had a calcium/phosphate ratio of 1.57 (average of 3 measurements±S.D.).

(4) Non-Mineral Content (Residual Organic Content)

Residual protein content was determined by analyzing the % nitrogen content in the mineral product by the combustion method. Result of the analysis was recorded as weight of nitrogen found in the sample, and % nitrogen content was calculated. The residual protein content was calculated based on the assumption that the average nitrogen content in protein is 13.6% w/w (derived by dividing the average weight of nitrogen in all amino acids by the average molecular weight of all amino acids). In addition, the methanol extractable content was applied to determine the lipid content in bone mineral product. It was determined that the bone mineral had a protein content of 0.75±0.08% and a methanol extractable of 0.03±0.01% (average of 6 measurements±S.D.)

(5) In Vivo Study

An animal study was performed in a rabbit femoral defect model to evaluate the biocompatibility and efficacy of the derived natural carbonate apatite bone mineral prepared above. Nine animals were implanted with the bone mineral. They were sacrificed at 4, 8, and 14 weeks. Histologically, the implanted mineral showed bone ingrowth as evidenced by new bone and bone marrow formation. There was no sign of any safety issue, as there was a lack of inflammation and a low number of giant cells associated with the implant mineral at all time points. It was concluded that the mineral product is biocompatible, osteoconductive without any significant unwanted tissue reaction.

Preparation of Porcine Carbonate Apatite Bone Mineral

Porcine bone particles were subjected to a series of water and isopropyl alcohol (IPA) rinses to remove loose adhering tissue, lipids, and lipoproteins. More specifically, the porcine bone particles were extracted with $H_2O$ at 100° C. for 1.5 h, which was repeated three more times. The washed porcine bone particles were then extracted with 100% IPA at 22±3° C. for 17±1 h. Subsequently, three extractions with $H_2O$ at 100° C. were performed for 2 h per extraction, followed by a second extraction with 100% IPA at 22±3° C. for 17±1 h. Optionally, the porcine bone particles can be washed three times with $H_2O$ at 22±3° C. for 3 h, 3 h, and 18 h prior to the first extraction.

The cleaned porcine bone particles were then heat treated at 585-600° C. for 37±2 h, followed by 250±10° C. for 4±1 h. The series of cleaning and heat treatment serves to remove the most of organic components from the bone leaving behind the calcium phosphate mineral component of the bone.

Prior to storage or analysis, the porcine carbonate apatite bone mineral was washed with 0.2 M phosphate buffer at 22±3° C. for 24 h and then oven dried.

The porcine carbonate apatite bone mineral thus prepared had a residual protein content of 5982±2246 parts per million and a surface area of 45.96 m²/g.

Preparation of Bovine Carbonate Apatite Bone Mineral

Bovine bone particles were extracted with $H_2O$ at 100° C. for 1.5 h, which was repeated three more times. The washed bovine bone particles were then extracted with 100% IPA at 22±3° C. for 17±1 h. Subsequently, three extractions with $H_2O$ at 100° C. were performed for 2 h per extraction, followed by a second extraction with 100% IPA at 22±3° C. for 17±1 h.

The cleaned bovine bone particles were then heat treated at 593-603° C. for 36±2 h, followed by 250±10° C. for 4±1 h.

Prior to storage or analysis, the bovine carbonate apatite bone mineral was washed with 0.2 M phosphate buffer at 22±3° C. for 24 hours and then oven dried.

The bovine carbonate apatite bone mineral thus prepared had a residual protein content of 4687±1750 parts per million and a surface area of 25.96 m²/g.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

The invention claimed is:

1. A carbonate apatite prepared from natural bone, the carbonate apatite having a surface area of 15 to 70 m²/g and a protein content of 2000-8000 parts per million.

2. The carbonate apatite of claim 1, wherein the carbonate apatite has a carbonate content of 1 to 7%.

3. The carbonate apatite of claim 2, wherein the carbonate apatite has a degree of crystallinity of 45 to 65%.

4. The carbonate apatite of claim 1, wherein the carbonate apatite has a degree of crystallinity of 45 to 65%.

5. A carbonate apatite prepared from natural bone by the steps consisting of:
   providing cancellous bone particles;
   treating the bone particles with hot water and an organic solvent;
   repeating the treating step at least once;
   drying the treated bone particles; and
   heating the treated dried bone particles at 570° C. to 610° C. for 10 to 40 hours,
   wherein the carbonate apatite has a surface area of 15 to 70 m²/g and a protein content of 2000-8000 parts per million.

6. The carbonate apatite of claim 5, wherein the carbonate apatite has a carbonate content of 1 to 7%.

7. The carbonate apatite of claim 6, wherein the carbonate apatite has a degree of crystallinity of 45 to 65%.

8. The carbonate apatite of claim 5, wherein the carbonate apatite has a degree of crystallinity of 45 to 65%.

9. The carbonate apatite of claim 5, wherein the organic solvent is isopropanol.

10. The carbonate apatite of claim 8, wherein the organic solvent is isopropanol.

11. The carbonate apatite of claim 5, wherein the temperature of the hot water is 80° C. to 100° C.

12. The carbonate apatite of claim 8, wherein the temperature of the hot water is 80° C. to 100° C.

13. The carbonate apatite of claim 6, wherein the organic solvent is isopropanol.

14. The carbonate apatite of claim 7, wherein the organic solvent is isopropanol.

15. The carbonate apatite of claim 6, wherein the temperature of the hot water is 80° C. to 100° C.

16. The carbonate apatite of claim 7, wherein the temperature of the hot water is 80° C. to 100° C.

* * * * *